(12) United States Patent
Liu et al.

(10) Patent No.: US 7,287,431 B2
(45) Date of Patent: Oct. 30, 2007

(54) WIRELESS OIL FILTER SENSOR

(75) Inventors: James Z T Liu, Belvidere, IL (US); Michael L. Rhodes, Richfield, MN (US); Aziz Rahman, Sharon, MA (US)

(73) Assignee: Honeywell International Inc., Morristown, NJ (US)

( * ) Notice: Subject to any disclaimer, the term of this patent is extended or adjusted under 35 U.S.C. 154(b) by 182 days.

(21) Appl. No.: 11/107,099

(22) Filed: Apr. 14, 2005

(65) Prior Publication Data
US 2006/0230833 A1 Oct. 19, 2006

(51) Int. Cl.
*G01N 29/036* (2006.01)

(52) U.S. Cl. .................. 73/649; 73/53.05; 73/54.01; 73/54.25

(58) Field of Classification Search .............. 73/649, 73/703, 702, 704, 768, 598, 19.11, 54.01, 73/19.03, 53.05, 54.24, 54.25, 54.38, 54.41
See application file for complete search history.

(56) References Cited

U.S. PATENT DOCUMENTS

| | | | |
|---|---|---|---|
| 4,691,714 A | 9/1987 | Wong et al. | ............ 128/738 |
| 4,782,332 A | 11/1988 | Cipris et al. | ............ 340/603 |
| 4,792,791 A | 12/1988 | Cipris et al. | ............ 340/603 |
| 5,235,235 A | 8/1993 | Martin et al. | ......... 310/313 D |
| 5,274,335 A | 12/1993 | Wang et al. | ............ 324/689 |
| 5,301,643 A | 4/1994 | Garcyalny | ............ 123/198 D |
| 5,336,396 A | 8/1994 | Shetley | ............ 210/90 |
| 5,821,425 A * | 10/1998 | Mariani et al. | ............ 73/703 |
| 5,869,763 A | 2/1999 | Vig et al. | ............ 73/580 |
| 5,878,708 A | 3/1999 | Ruman | ............ 123/196 M |
| 6,023,961 A | 2/2000 | Discenzo et al. | |
| 6,044,332 A | 3/2000 | Korsah et al. | ............ 702/76 |
| 6,076,406 A | 6/2000 | Blair et al. | ............ 73/590 |
| 6,278,282 B1 * | 8/2001 | Marszalek | ............ 324/663 |
| 6,293,136 B1 | 9/2001 | Kim | ............ 73/19.03 |

(Continued)

FOREIGN PATENT DOCUMENTS

WO WO 2005/040788 5/2005

OTHER PUBLICATIONS

Reindl L. et al., Saw Devices as Wireless Passive Sensors, IEEE Ultrasonics Symposium, 1996, vol. 1, pp. 363-367, Nov. 3, 1996, New York, NY.

(Continued)

*Primary Examiner*—Hezron Williams
*Assistant Examiner*—Jacques M. Saint-Surin
(74) *Attorney, Agent, or Firm*—Kermit D. Lopez; Luis M. Ortiz; William B. Shelby

(57) ABSTRACT

A wireless oil filter sensing system includes an oil filter and a sensing mechanism that is connectable to the oil filter. The sensing mechanism includes one or more acoustic wave sensing elements and at least one antenna that communicate with the acoustic wave sensing element(s). An external interrogation system could excite the acoustic wave sensing element(s) wireless and passively. When the acoustic wave sensing elements are in contact with oil contained in the oil filter, the acoustic wave sensing elements detect acoustic waves associated with the oil in response to an excitation of the acoustic wave sensing elements, thereby generating data indicative of the quality of the oil for wireless transmission through the antenna(s).

21 Claims, 10 Drawing Sheets

U.S. PATENT DOCUMENTS

| | | | |
|---|---|---|---|
| 6,459,995 B1 * | 10/2002 | Collister | 702/23 |
| 6,508,100 B2 | 1/2003 | Berndorfer | 73/1.02 |
| 6,557,396 B2 | 5/2003 | Ismail et al. | 73/53.05 |
| 6,776,024 B2 | 8/2004 | Jakoby | 73/10 |
| 6,786,080 B2 | 9/2004 | Jakoby et al. | 73/54.04 |
| 6,799,458 B2 | 10/2004 | Ismail et al. | 73/304 C |
| 7,043,969 B2 * | 5/2006 | Matsiev et al. | 73/54.41 |
| 7,134,319 B2 * | 11/2006 | Liu | 73/31.06 |
| 7,136,683 B2 * | 11/2006 | Eisenhower et al. | 455/575.1 |
| 7,219,536 B2 * | 5/2007 | Liu et al. | 73/54.24 |
| 2004/0035398 A1 | 2/2004 | Klugl et al. | 123/456 |
| 2004/0099050 A1 | 5/2004 | Matsiev et al. | |
| 2004/0123644 A1 * | 7/2004 | Jakoby et al. | 73/19.11 |
| 2005/0110599 A1 * | 5/2005 | Kanasaki et al. | 333/193 |
| 2006/0254356 A1 * | 11/2006 | Liu et al. | 73/592 |
| 2006/0272415 A1 * | 12/2006 | Liu et al. | 73/592 |
| 2006/0283249 A1 * | 12/2006 | Liu et al. | 73/579 |
| 2007/0074563 A1 * | 4/2007 | Liu et al. | 73/54.24 |
| 2007/0107519 A1 * | 5/2007 | Liu et al. | 73/649 |

OTHER PUBLICATIONS

Hammond J.M. et al., An Acoustic Automotive Engine Oil Quality Sensor, IEEE Frequency Control Symposium, 1997, pp. 72-80, May 28-30, 1997, New York, NY.

Grate and Frye, Acoustic Wave Sensors Update, 1996, pp. 37-83.

B. Jakoby, M. Scherer, M. Buskies, H. Eisenschmid; *An Automotive Engine Oil Viscosity Sensor* IEEE Sensors Journal vol. 3 No. 5 Oct. 2003.

R.M. Lee, X.J. Zhang, J.M. Hammond; *A Remote Acoustic Engine Oil Quality Sensor* Dept. of Electrical & Computer Engineering, University of Maine, 1997 IEEE Ultrasonics Symposium.

X. Zhang; *An On-Board Automobile Engine Oil Quality Sensor* Thesis, The Graduate School University of Maine, Aug. 1998.

\* cited by examiner

WIRELESS OIL FILTER SENSOR

TECHNICAL FIELD

Embodiments are generally related to sensing devices and components thereof. Embodiments also relate to oil quality detection inside an oil filter. Embodiments additionally relate to different types of acoustic waves devices, such as shear horizontal surface acoustic wave (SH-SAW), flexural plate wave (FPW), Love mode, acoustic plate mode (APM), shear horizontal acoustic plate mode (SH-APM), and bulk acoustic waves (BAW), including thickness shear mode, torsional mode, and flexural mode components and devices thereof. Embodiments additionally relate to the wireless transmission of detection data.

BACKGROUND OF THE INVENTION

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, they are also used for chemical vapor detection. Acoustic wave sensors are so named because they use a mechanical, or acoustic, wave as the sensing mechanism. As the acoustic wave propagates through or on the surface of the material, any changes to the characteristics of the propagation path affect the velocity and/or amplitude of the wave.

Changes in acoustic wave characteristics can be monitored by measuring the frequency or phase characteristics of the sensor and can then be correlated to the corresponding physical quantity or chemical quantity that is being measured. Virtually all acoustic wave devices and sensors utilize a piezoelectric crystal to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the SAW sensor.

Examples of acoustic wave sensors include acoustic wave detection devices, which are utilized to detect the presence of substances, such as chemicals, or environmental conditions such as temperature and pressure. An acoustical or acoustic wave (e.g., SAW/BAW) device acting as a sensor can provide a highly sensitive detection mechanism due to the high sensitivity to surface loading and the low noise, which results from their intrinsic high Q factor. Surface acoustic wave devices are typically fabricated using photolithographic techniques with comb-like interdigital transducers placed on a piezoelectric material. Surface acoustic wave devices may have either a delay line or a resonator configuration. Bulk acoustic wave device are typically fabricated using a vacuum plater, such as those made by CHA, Transat or Saunder. The choice of the electrode materials and the thickness of the electrode are controlled by filament temperature and total heating time. The size and shape of electrodes are defined by proper use of masks.

Based on the foregoing, it can be appreciated that acoustic wave devices, such as a surface acoustic wave resonator (SAW-R), surface acoustic wave delay line (SAW-DL), surface transverse wave (STW), bulk acoustic wave (BAW), can be utilized in various sensing measurement applications. One of the primary differences between an acoustic wave sensor and a convention sensor is that an acoustic wave sensor can store energy mechanically. Once such a sensor is supplied with a certain amount of energy (e.g., through RF), the sensor can operate for a time without any active part (e.g., without a power supply or oscillator). This feature makes it possible to implement an acoustic wave sensor in an RF powered passive and wireless sensing application.

One promising application for micro-sensors involves oil filter and oil quality monitoring. Low temperature startability, fuel economy, thinning or thickening effects at high and/or low temperatures, along with lubricity and oil film thickness in running automotive engines are all dependent upon viscosity. Therefore, viscosity should be the best indicator of engine oil's ability to function properly. Frequency changes in viscosity have been utilized in conventional oil detection systems. The frequency changes caused by small changes in viscosity of highly viscous liquids, however, are very small. Because of the highly viscous loading, the signal from a sensor oscillator is very "noisy" and the accuracy of such measurement systems is very poor. Moreover, such oscillators may cease oscillation due to the loss of the inductive properties of the resonator.

Based on the foregoing it is believed that a solution to the problems associated with conventional oil micro-sensing applications may involve acoustic wave devices. Acoustic wave sensors are capable of functioning in a very sensitive state, because they can detect both mechanical and electrical property changes that include variations in mass, elasticity, dielectric properties and conductivity (e.g., electronic, ionic and thermal). This is because the acoustic wave that probes the medium of interest has both mechanical displacements and an electric field. Such a feature stands in contrast to many other micro-sensor technologies that usually monitor a change in a single material property. Therefore, it is believed that acoustic wave sensors may well be suited for monitoring the visco-elastic property of engine oil as indicated by the embodiments described herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensing device.

It is another aspect of the present invention to provide for an acoustic wave sensing device adapted for oil filter detection.

It is yet another aspect of the present invention to provide for a wireless oil sensor.

The aforementioned aspects and other objectives and advantages can now be achieved as described herein. A wireless oil filter sensing system is described. Such a system includes an engine oil filter and a sensing mechanism that is connectable to the oil filter. The sensing mechanism includes one or more acoustic wave sensing elements and an antenna that communicates with the acoustic wave sensing element(s). The acoustic wave sensing element(s) could be excited by an external interrogator which includes a receiver and a transmitter. When the acoustic wave sensing elements are in contact with oil contained in the oil filter, the acoustic wave sensing elements detect acoustic waves associated with the oil in response to an excitation of the wave sensing elements, thereby generating data indicative of the quality of the oil for wireless transmission through the antenna.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
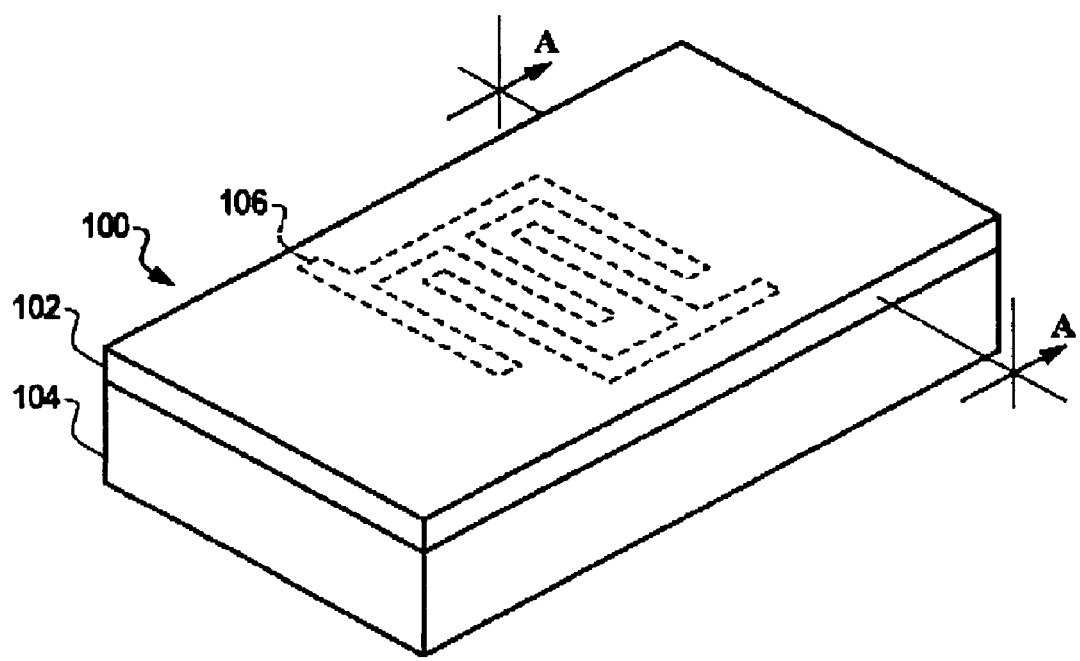
FIG. 1 illustrates a perspective view of an interdigital surface wave device, which can be implemented in accordance with one embodiment.

FIG. 1 illustrates a perspective view of an interdigital surface wave device 100, which can be implemented in accordance with one embodiment. Shear horizontal surface wave device (SH-SAW) 100 generally includes an interdigital transducer 106 formed on a piezoelectric substrate 104. The surface wave device 100 can be implemented in the context of a sensor chip. Interdigital transducer 106 can be configured in the form of an electrode, depending upon design considerations.

Note that the interdigital surface wave device 100 represents only one type of acoustic wave device that can be adapted for use with the embodiments disclosed herein. It can be appreciated that a variety of other types (e.g., SH-SAW, BAW, APM, SH-APM, FPW, SH-SAW-DL, SH-SAW-R, etc.) can be utilized in accordance with the embodiments described herein. Additionally, acoustic wave device 100 can be implemented in a variety of shapes and sizes.

By correctly selecting the orientation of material cut, shear-horizontal surface acoustic waves (SH-SAW) will dominate. These waves have a displacement that is parallel to the device's surface. If the cut of the piezoelectric crystal material is rotated appropriately, the wave propagation mode changes from a vertical shear SAW sensor to a shear-horizontal SAW sensor. This dramatically reduces loss when liquids come into contact with the propagating medium, allowing the SH-SAW sensor to operate in liquids as a chemical or biosensor.

Shear-Horizontal Surface Acoustic Wave (SH-SAW) devices use a piezoelectric substrate with metal interdigital transducers electrodes (IDTs or IDEs) deposited on one of the surfaces. Application of an oscillatory voltage to the IDT generates a displacement of the surface. The displacement "wave" will propagate away from the IDT. If the wave propagates to a second IDT placed a distance away, we form a "delay line" device. A key issue for operating surface wave devices in liquids is to generate surface displacements that are shear in direction. Thus, the wave displacement is perpendicular to the direction of wave propagation and in the plane of the crystal surface. The crystal cut of the piezoelectric substrate must be chosen so that application of the electric field by the IDTs produces a shear surface motion.

Figure 2:
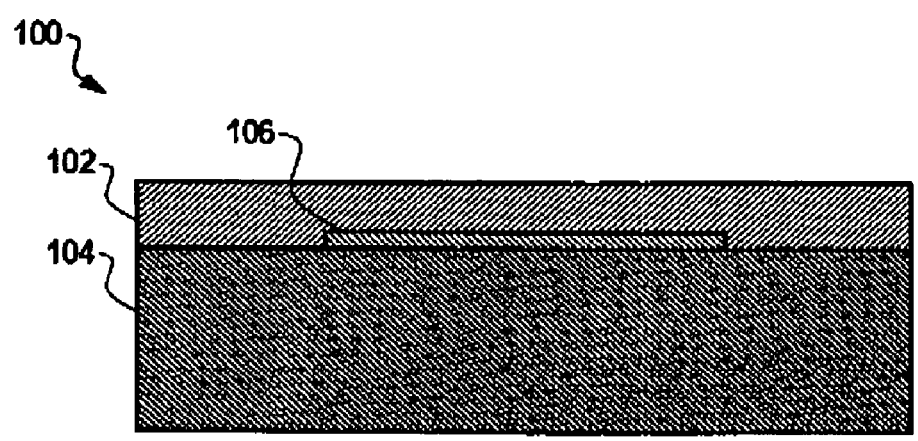
FIG. 2 illustrates a cross-sectional view along line A-A of the interdigital surface wave device depicted in FIG. 1, in accordance with one embodiment.

FIG. 2 illustrates a cross-sectional view along line A-A of the interdigital surface wave device 100 depicted in FIG. 1, in accordance with one embodiment of the present invention. Piezoelectric substrate 104 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few. Interdigital transducer 106 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAl. Third, interdigital transducer 106 can be formed from metal-nonmetal compounds (e.g., ceramic electrodes based on TiN, $CoSi_2$, or WC).

The coating 102 need not cover the entire planar surface of the piezoelectric substrate 104, but can cover only a portion thereof, depending upon design constraints. Coating 102 can function as a protecting layer or a guiding layer, which is shown in greater detail herein with respect to FIG. 5. Selective coating 102 can cover interdigital transducer 106 and the entire planar surface of piezoelectric substrate 104. The interdigital surface wave device 100 may function as a multiple mode sensing device, excited multiple modes thereof generally occupy the same volume of piezoelectric material. Multiple modes excitation allows separations of temperature change effects from pressure change effects. The multi-mode response can be represented by multiple mode equations, which can be solved to separate the response due to the temperature and pressure.

Figure 3:
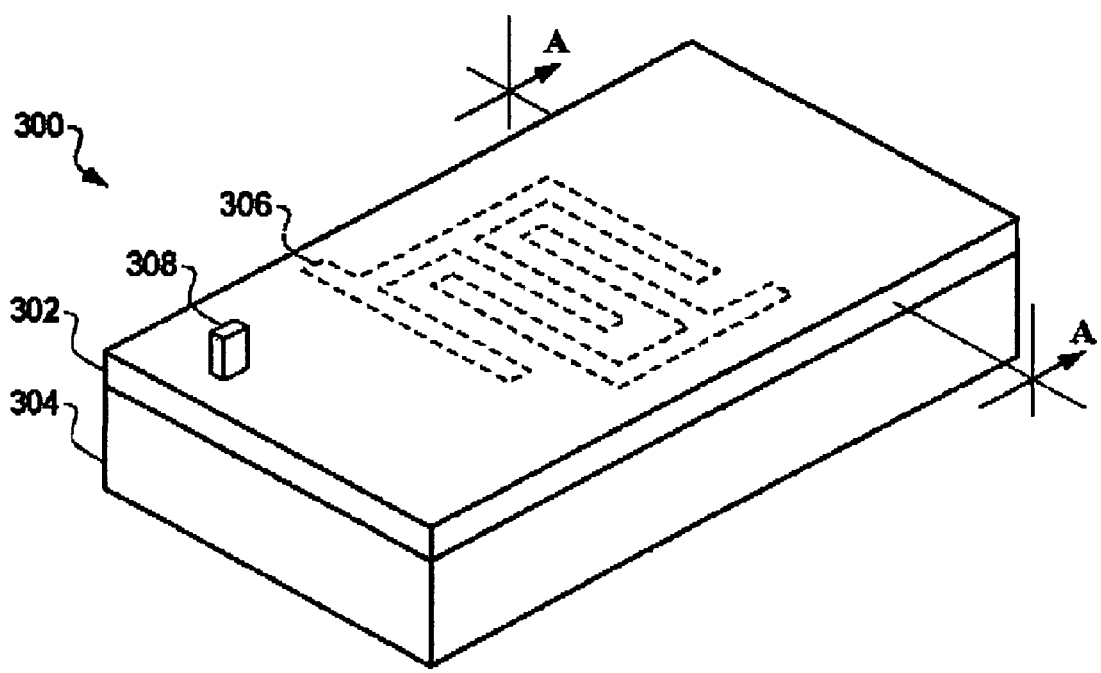
FIG. 3 illustrates a perspective view of an interdigital surface wave device, which can be implemented in accordance with an embodiment.
Figure 4:
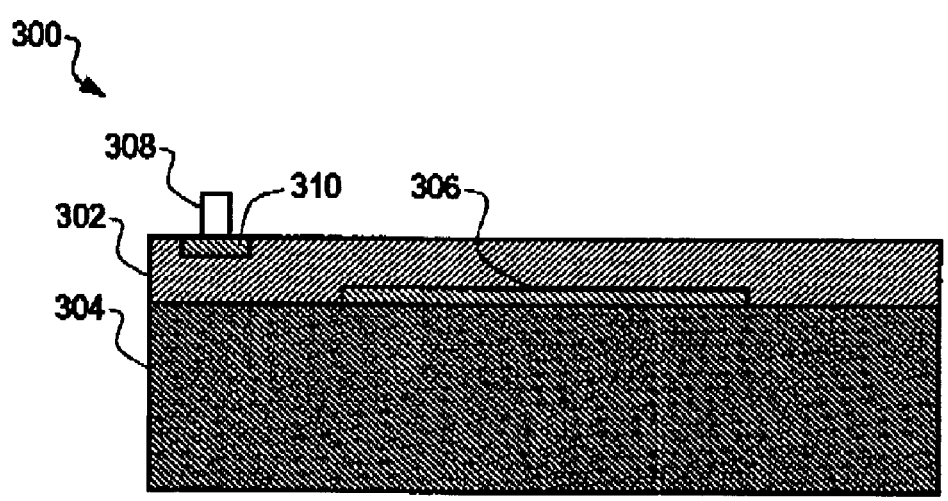
FIG. 4 illustrates a cross-sectional view along line A-A of the interdigital surface wave device depicted in FIG. 3, in accordance with one embodiment.

FIG. 3 illustrates a perspective view of an interdigital surface wave device 300, which can be implemented in accordance with an embodiment. The configuration depicted in FIGS. 3-4 is similar to that illustrated in FIGS. 1-2, with the addition of an antenna 308, which is connected to and disposed above a wireless excitation component 310 (i.e., shown in FIG. 4). The antenna 308 can be, for example, a linear type antenna, or a coupler type antenna depending upon design considerations. Surface wave device 300 generally includes an interdigital transducer 306 formed on a piezoelectric substrate 304.

Surface wave device 300 can therefore function as an interdigital surface wave device, and one, in particular, which utilizes surface-skimming bulk wave techniques. Interdigital transducer 306 can be configured in the form of an electrode. A coating 302 can be selected such that a particular species to be measured is absorbed by the coating 302, thereby altering the acoustic properties of the interdigital surface wave device 300. Various selective coatings can be utilized to implement coating 302.

A change in acoustic properties can be detected and utilized to identify or detect the substance or species absorbed and/or adsorbed by the coating 302. Thus, the interdigital surface wave device 300 can be excited via wireless means to implement a surface acoustical model. Thus, antenna 308 can be utilized to excite multiple modes, thereby allowing separation of temperature change effects from pressure change effects. Such an excitation can produce a variety of other modes of interdigital surface wave device 300.

FIG. 4 illustrates a cross-sectional view along line A-A of the interdigital surface wave device 300 depicted in FIG. 3, in accordance with one embodiment of the present invention. Thus, antenna 308 is shown in FIG. 4 disposed above coating 302. Similar to the configuration of FIG. 2, Piezoelectric substrate 304 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few. Interdigital transducer 306 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAl. Third, interdigital transducer 306 can be formed from metal-nonmetal compounds (e.g., ceramic electrodes based on TiN, $CoSi_2$, or WC).

Figure 5:
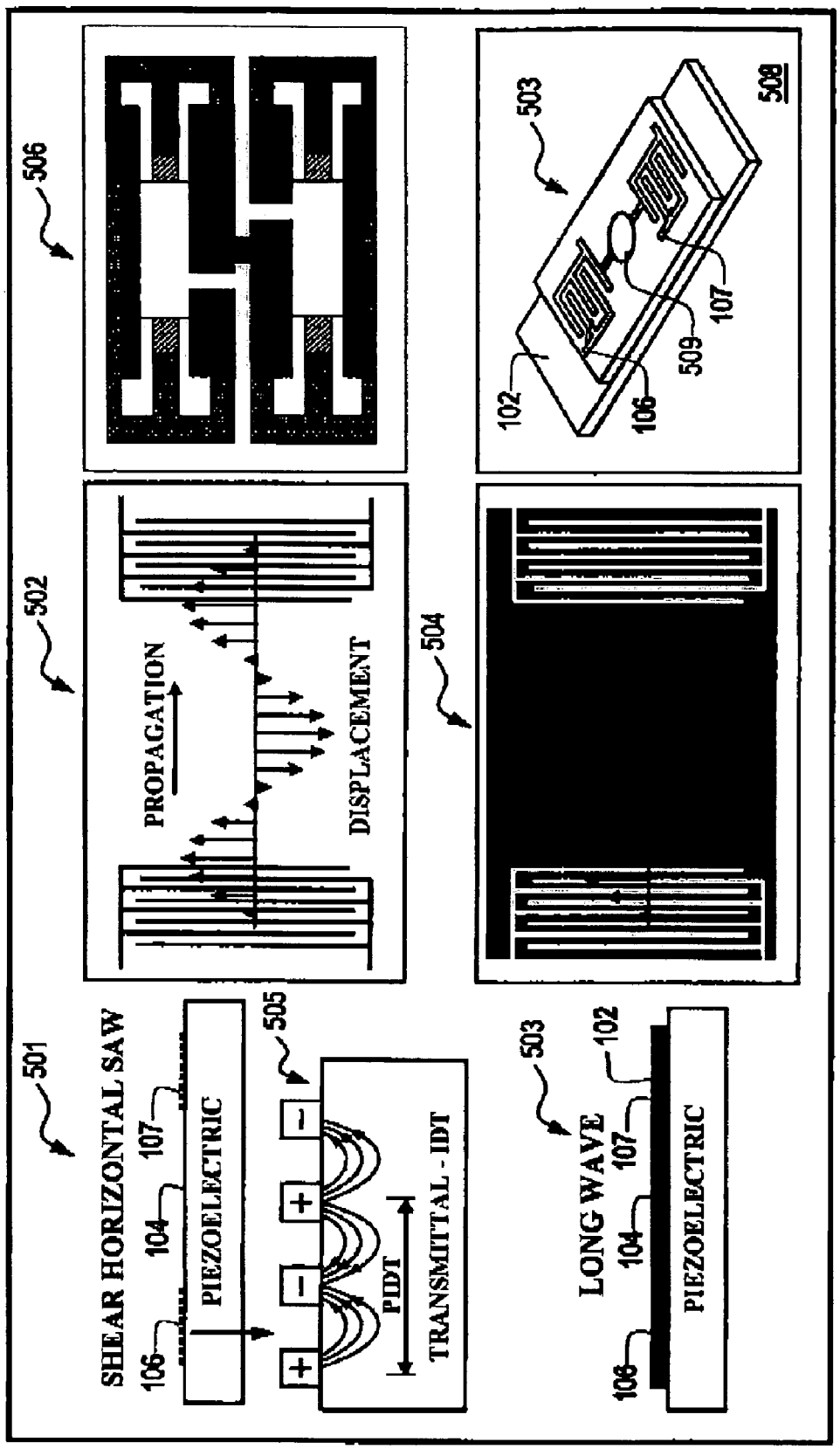
FIG. 5 illustrates side, perspective and top views of an SH-SAW and Love mode devices that can be adapted for use in accordance with the embodiments disclosed herein.

FIG. 5 illustrates side, perspective and top views of an SH-SAW device that can be adapted for use in accordance with the embodiments disclosed herein. Note that in FIGS. 1-5, identical or similar parts or elements are generally indicated by identical reference numerals. Varying configurations are depicted in FIG. 5. For example, a shear horizontal (SH) SAW device 501 is depicted in association with a transmitter IDT device 505. Shear horizontal (SH) SAW device 501 generally includes piezoelectric substrate 104 and interdigital transducers 106, 107. A graph 502 indicating propagation and displacement thereof is also illustrated in FIG. 5 in association with shear horizontal (SH) SAW device 501. A love wave device 503 is also depicted in FIG. 5, which includes piezoelectric substrate 104, interdigital transducers 106, 107 and a guiding layer 102 (i.e., a coating). A graph 504 is associated with love wave device 503, also depicting general propagation and displacement thereof. A top view 506 of the love wave device 104 is also depicted in FIG. 5, along with a perspective view 508 of love wave device 104. Love wave 509 is also depicted in perspective view 508.

Figure 6:
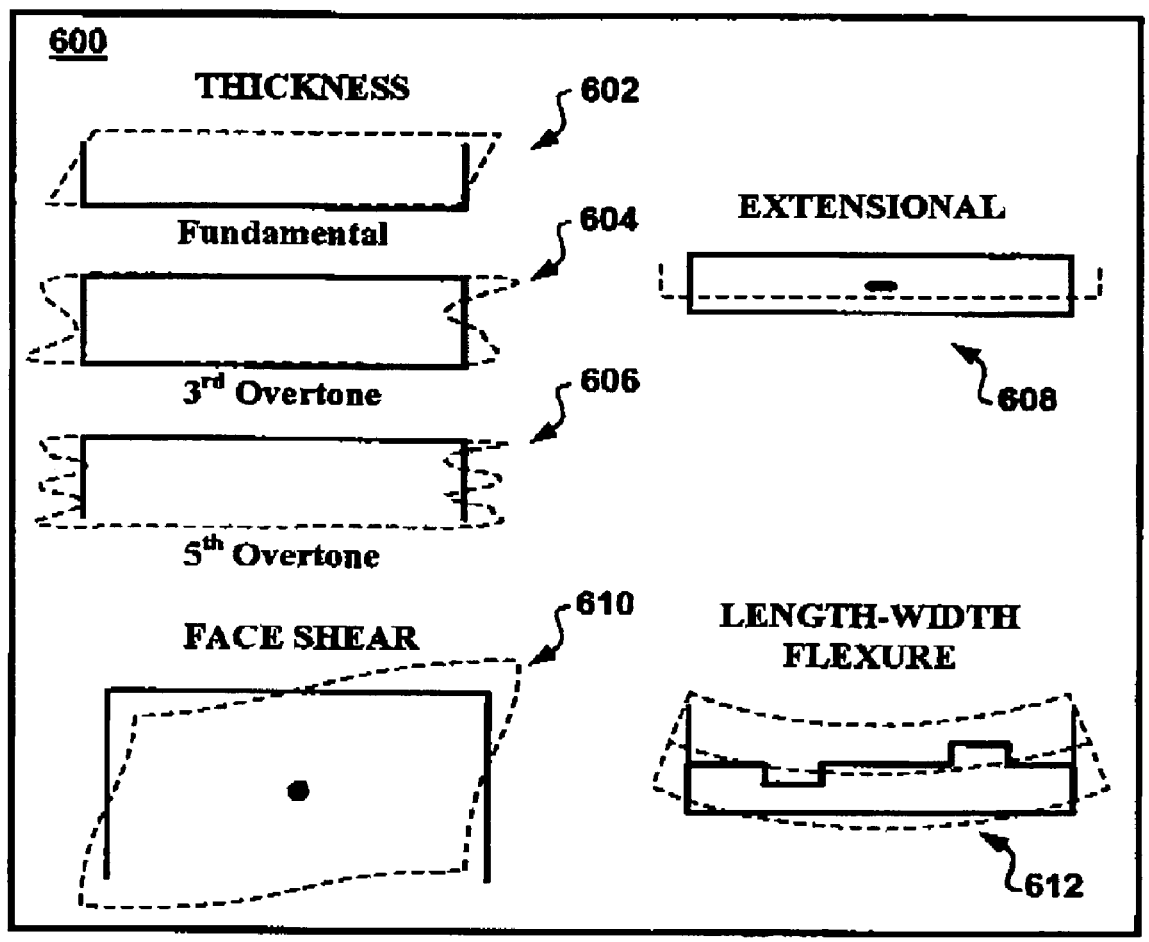
FIG. 6 illustrates multiple modes that can exist in a wireless oil sensor, in accordance with one embodiment.

FIG. 6 illustrates multiple modes 600 that can exist in a wireless oil sensor (e.g., see system 700 depicted in FIG. 7) as described herein. As indicated in FIG. 6, example modes 600 can include one or more thickness modes, including fundamental 602, $3^{rd}$ overtone 604, and $5^{th}$ overtone 605 modes. An extensional mode 608 is also depicted in FIG. 6, along with a face shear mode 610 and a length-width fixture mode 612. It can be appreciated that one or more of such modes can be adapted for use in accordance with one or more embodiments. Modes 600 depicted in FIG. 6 can therefore be considered in the implementation of an oil filter sensing system, such as, for example, system 700 depicted in FIG. 7.

Figure 7:
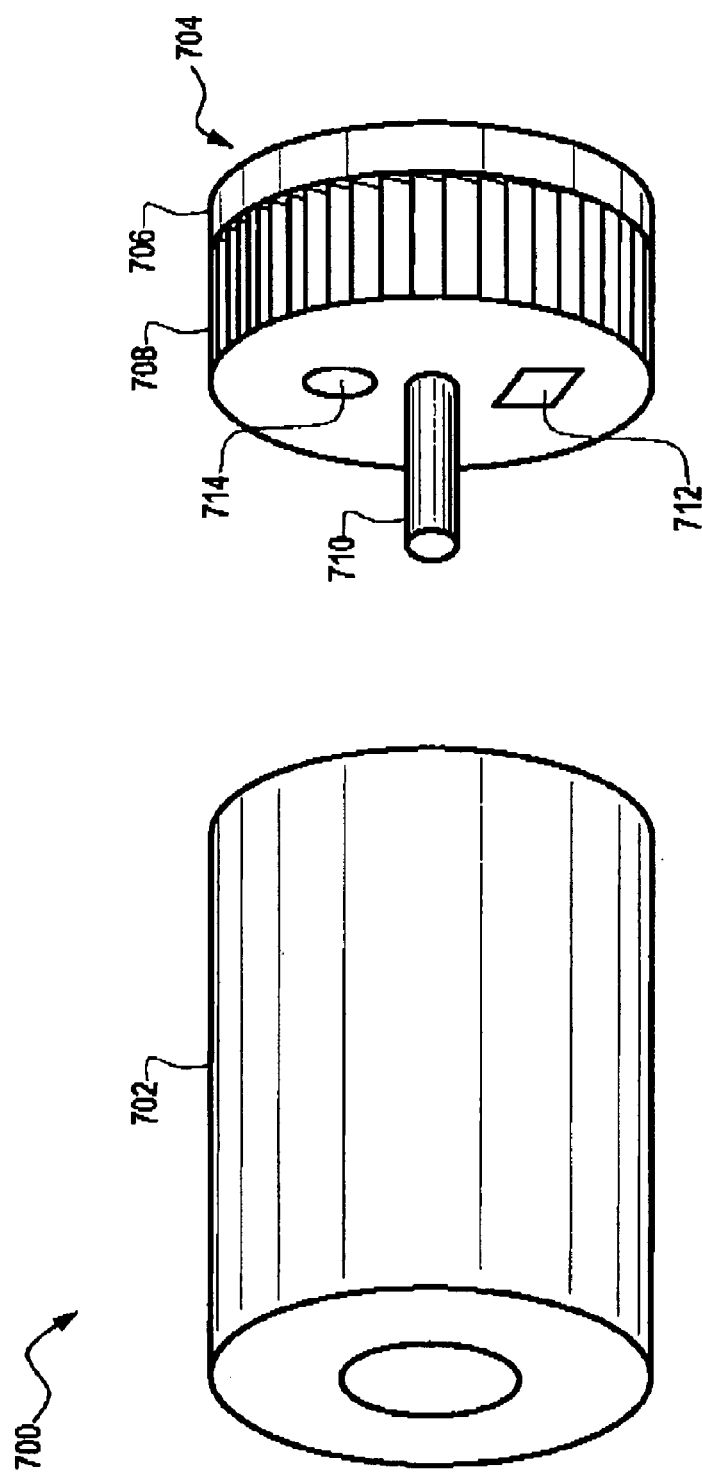
FIG. 7 illustrates a wireless oil filter sensing system that can be implemented in accordance with one embodiment.

FIG. 7 illustrates a wireless oil filter sensing system 700 that can be implemented in accordance with one embodiment. System 700 generally includes an oil filter 702 and a sensing mechanism 704 that is connectable to the oil filter 702. The sensing mechanism 704 can be configured to comprise one or more acoustic wave sensing elements 712, 714 and an antenna 706 that communicates with the acoustic wave sensing elements 712, 714. Note that the acoustic wave sensing elements 712, 714 can be implemented, for example, as BAW, SH-SAW, SH-APM, FPW components. Antenna 706 can be implemented, for example, in a manner similar to that of antenna 308 depicted in FIG. 3. The antenna could be a linear type or a coupler type. The surface wave device 100 depicted in FIGS. 1-4, for example, can be utilized to implement surface acoustic wave sensing elements 712, 714, depending upon design considerations.

When the acoustic wave sensing elements 712, 714 are in contact with oil contained in the oil filter 702, the acoustic wave sensing elements 712, 714 can detect acoustic waves associated with the oil thereof in response to an excitation of the acoustic wave sensing elements 712, 714, thereby generating data indicative of a quality of the oil for wireless transmission through the antenna 706. The excitation of the acoustic wave sensing elements 712, 714 can occur in response to at least one wireless signal transmitted to the antenna. The acoustic waves associated with the oil can comprise bulk wave and shear-horizontal surface acoustic waves. Note that sensing mechanism 704 can be configured to incorporate a screw 710 or another type of connector for connecting to oil filter 702 for sensing operations thereof.

Figure 8:
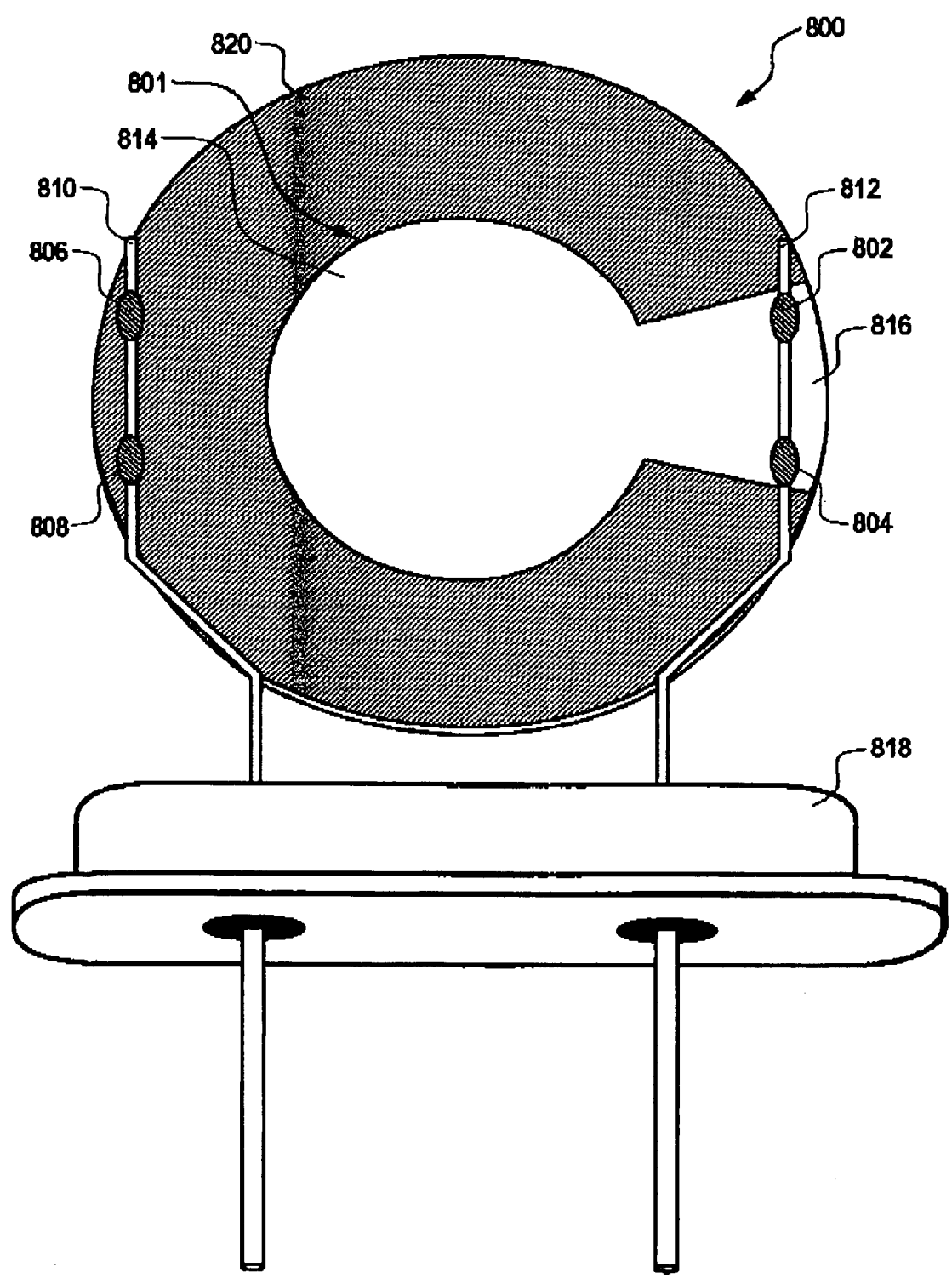
FIG. 8 illustrates a pictorial diagram of a BAW engine oil quality sensor that can be utilized in accordance with one embodiment.

FIG. 8 illustrates a pictorial diagram of a BAW engine oil quality sensor 800 that can be utilized in accordance with one embodiment. Sensor 800 includes a BAW sensing element 801 composed of BAW portions 814 and 816. BAW portion 816 is connected to an electrically conducting contact 812 by connectors 802, 804, which may be, for example, solder. BAW sensing element 801 is formed on a substrate 820, which is connected to an electrically conducting contact 810 by connectors 806, 808, which may be, for example, solider. A platform 818 can be utilized to maintain contacts 810, 812 in place. Sensor 800 can be adapted for use, for example, with system 700 and/or 900 depicted and described herein. For example, sensor 800 depicted in FIG. 8 can be utilized to implement surface acoustic wave sensing elements 712, 714.

Figure 9:
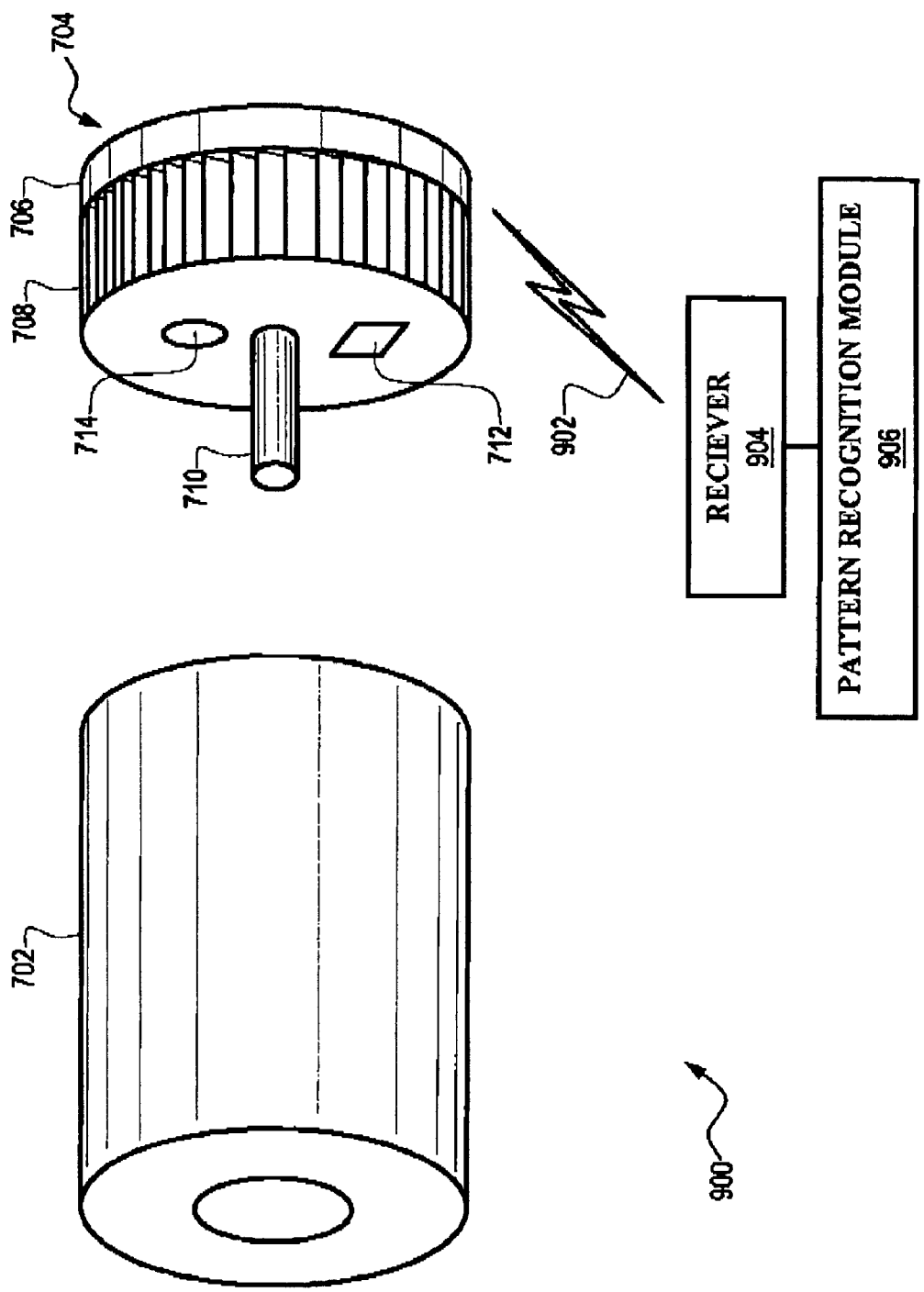
FIG. 9 illustrates a wireless oil filter sensing system that can be implemented in accordance with one embodiment.

FIG. 9 illustrates a wireless oil filter sensing system 900 that can be implemented in accordance with one embodiment. Note that in FIGS. 8 and 9, identical or similar parts are generally indicated by identical reference numerals. Thus, system 900 incorporates all of the components of system 700, and also includes a receiver 904 that can transmit and receive data to and antenna 706. Receiver 904 can also communicate with a pattern recognition module 906 that can be utilized to automatically recognize varying grades of oil and oil degradation processes.

Note that the pattern recognition module 906 can be implemented in the context of a "module". In the computer programming arts, a module can be typically implemented as a collection of routines and data structures that performs particular tasks or implements a particular abstract data type.

Modules generally can be composed of two parts. First, a software module may list the constants, data types, variable, routines and the like that that can be accessed by other modules or routines. Second, a software module can be configured as an implementation, which can be private (i.e., accessible perhaps only to the module), and that contains the source code that actually implements the routines or sub-routines upon which the module is based. Thus, for example, the term module, as utilized herein generally refers to software modules or implementations thereof. Such modules can be utilized separately or together to form a program product that can be implemented through signal-bearing media, including transmission media and recordable media.

Figure 10:
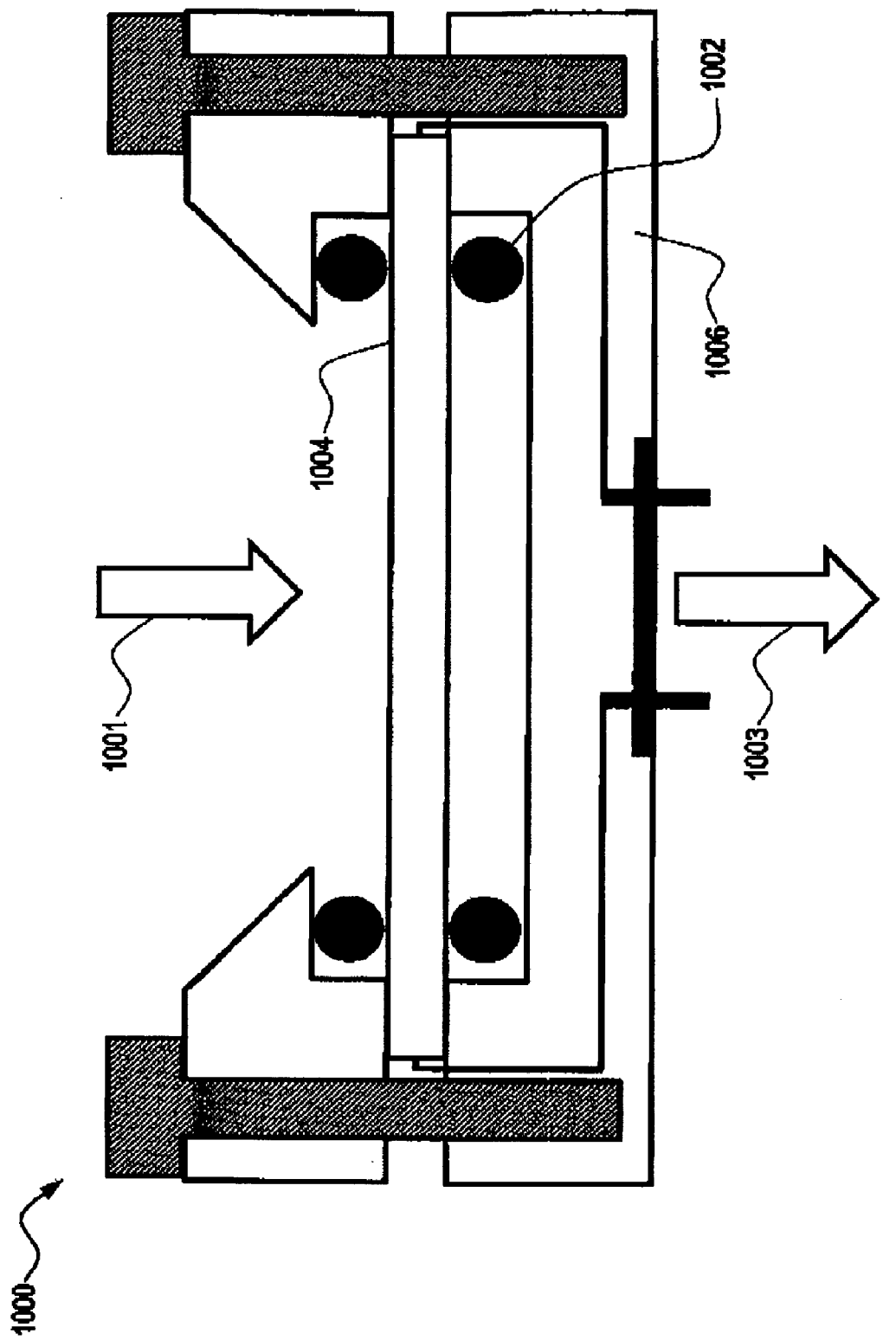
FIG. 10 illustrates a BAW viscosity sensor, with one electrode exposed to oil in accordance with alternative embodiment.

FIG. 10 illustrates a BAW viscosity sensor 1000, with one electrode exposed to oil in accordance with alternative embodiment. In general, BAW viscosity sensor 1000 includes a quartz component 1004 in association with an O-ring 1002 and a compartment 1006 thereof. Oil flows through sensor 1000 as indicated by arrows 1001, 1003. In general, a higher frequency SAW sensor will have higher sensitivity than its BAW counterpart because it is associated with a higher absolute frequency change for a given measurand. This is true, however, only if resolution is determined by the frequency measurement itself. The error of the frequency meter is determined by the digitizing uncertainty, the value of the time base, and by the accuracy of the time base.

Because SAW sensor stabilities are 2 orders worse than the time base accuracy, the resolution of a SAW frequency sensor is always determined by other factors, such as signal noise, rather than the frequency measurement itself. The higher frequency of a SAW device does not mean more usable sensitivity. For a fair comparison of sensors, the performance figure $S_Q$, $S_Q=SQ$. defined as product of reduced sensitivity S (frequency change caused by unit measurand quantity referred to the starting frequency), and resonator Q-value should be utilized. Such a formulation represents a general measure for the relevant stability and short term accuracy. The introduced $S_Q$ value is a simple abstract parameter that characterizes exclusively the sensor element performance. It is a sensor specific performance figure that dominantly determines the accuracy of the entire measurement system.

A BAW device such as sensor 1000 possesses many modes of motion (e.g., flexure mode, extensional mode, face shear mode, thickness shear mode, fundamental mode thickness shear, third overtone thickness shear.) For example, AT-cut and SC-cut resonators vibrate in the thickness shear mode. Above 100 MHz, overtone units that operate at a selected harmonic mode of vibration are often used (e.g., third overtone or 5th overtone). Higher than 100 MHz fundamental mode units can be manufactured by, e.g., chemical etching (diffusion controlled wet etching), plasma etching, and ion milling techniques.

Below 1 MHz, tuning forks, X-Y and NT bars (flexure mode), +5° X-cuts (extensional mode), or CT-cut and DT-cut units (face shear mode) can be used. Tuning forks have become the dominant type of low-frequency units due to their small size and low cost. The velocities of acoustic waves in solids are typically ~3,000 M/s (~$10^{-5}$ times the velocity of light). For the shear waves in AT-cut quartz, for example, the velocity of propagation in the thickness direction is 3,320 m/s; the fundamental mode frequency~v/2 h, where v is the acoustic wave velocity and h is the plate thickness. (e.g., thickness of the plate is one half the wavelength).

For BAW resonators, the plate thickness determines the fundamental-mode frequency. For SAW resonators, the inter-digital transducers' (IDT) spacings determine the frequency. For quartz, a 300 MHz BAW resonator plate is 6 μm thick. A 2.6 GHz SAW resonator has 0.4 μm IDT spacings, and can be produced by e-beam lithography.

Figure 11:
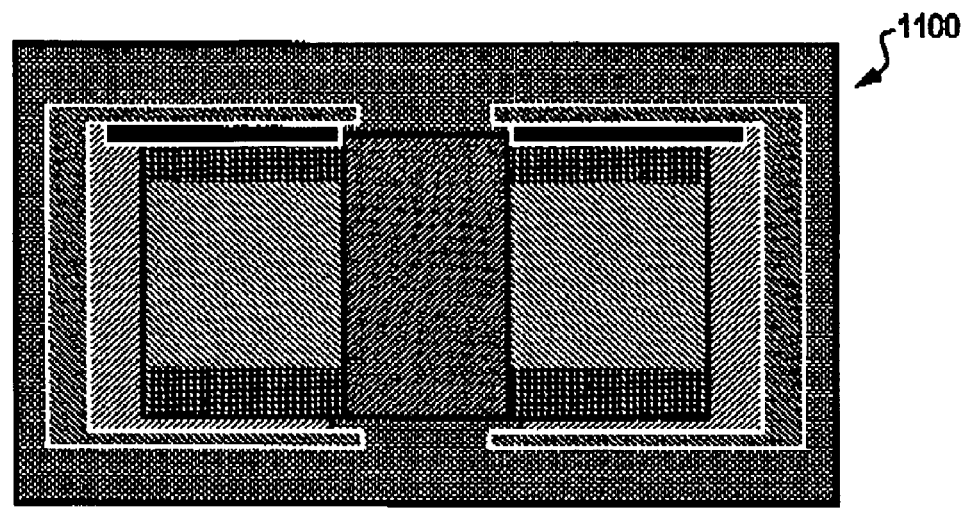
FIGS. 11 and 12 respectively illustrates a FPW viscosity sensor and an FPW sensor structure, which can be adapted for use with embodiments disclosed herein.
Figure 12:
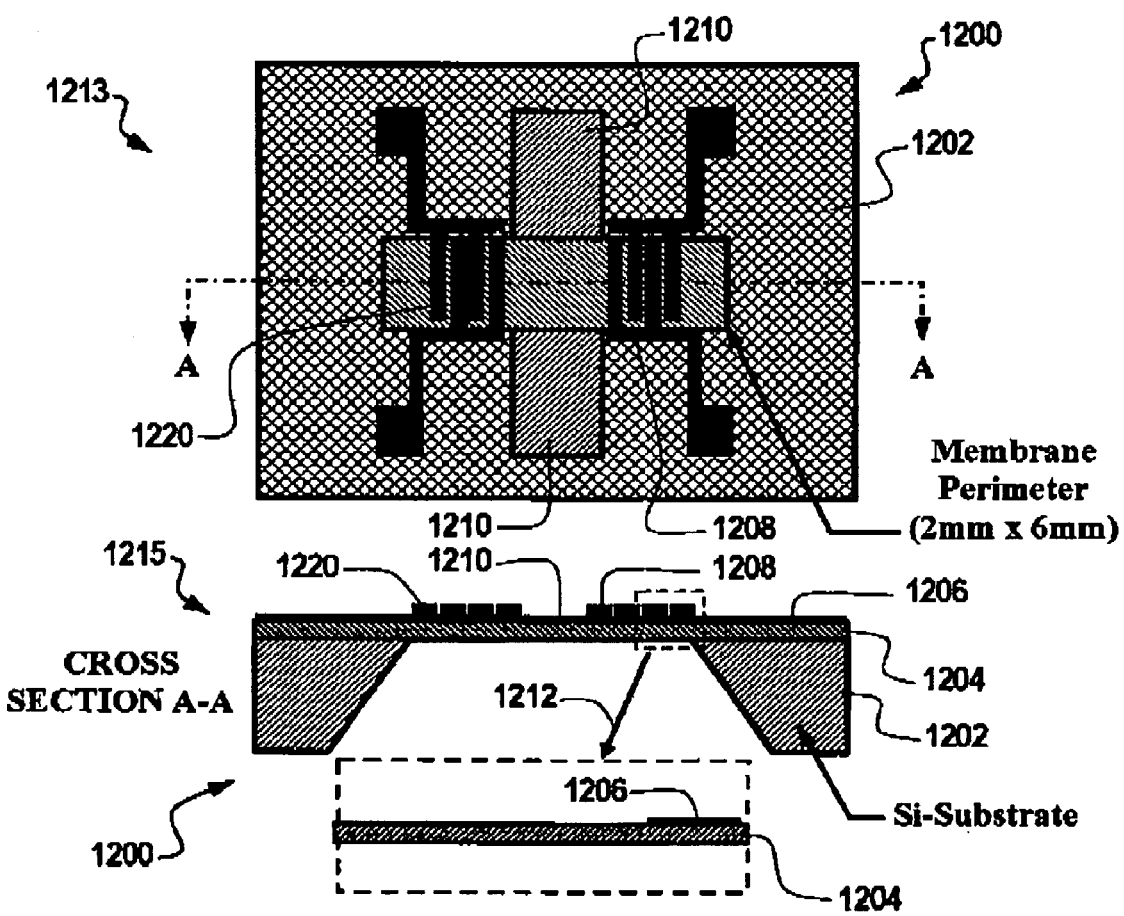

FIGS. 11 and 12 respectively illustrate a FPW viscosity sensor 1100 and an FPW sensor structure 1200, which can be adapted for use with embodiments disclosed herein. In a flexural plate wave (FPW) device, such as FPW viscosity sensor 1100, the acoustic wave is excited in a thinned membrane. The FPW viscosity sensor 1100 can detect quantities that cause its phase velocity to change. A unique feature of the FPW viscosity sensor 1100 is that it can be dimensioned so that Its phase velocity is lower than that of most liquids. When FPW is used in a liquid, a slow mode of propagation exists in which there is no radiation from the plate. Therefore, a FPW viscosity sensor 1100 is a good candidate for chemical and bio-sensing in liquids.

Because the plate of a FPW viscosity sensor 1100 could be as thin as a few μm, the sensitivity due to the mass loading is fairly high. Mass-loading causes the phase velocity of an acoustic wave propagating on the plate to decrease. The amplitudes of the displacements associated with a flexural wave of given total power are larger than other acoustic wave sensors. As a result of this large amplitude motion, the FPW viscosity sensor 1100 could be used as sensor and actuator in pumping and mixing of fluids.

The FPW viscosity sensor 1100 can be configured to employ IDT and piezoelectric coupling to generate and detect waves. A delay-line oscillator is usually formed for the FPW device. The frequencies employed in the FPW devices are usually 1 to 10 MHz, significantly lower than those used in SAW and APM. If it is desired to increase the sensitivity, the device should be made thinner, reducing the velocity (and incidentally reducing the frequency). This increased sensitivity with a lowered operating frequency is opposite to the situations in the TSM, SAW and APM devices. A practical chemical or biosensor based on FPW typically employs an adsorption film like those used for TSM, SAW and APM. The FPW viscosity sensor 1100 has 10 times higher sensitivity than that of a SH-APM sensor, but the FPW sensor suffers fragility.

An FPW sensor structure 1200 is depicted in FIG. 12 and can be utilized to implement a flexural plate wave (FPW) device, such as the FPW viscosity sensor 1100 depicted in FIG. 11. In FIG. 12, a top view 1213 of the micro-fabricated chip structure 1200 is illustrated. Additionally, a cross sectional view 1215 of the micro-fabricated chip structure 1200 is illustrated in FIG. 12. To fabricate flexural plate wave (FPW) devices, one begins with a standard silicon wafer or silicon substrate 1202. A membrane layer 1204 can be deposited on the substrate 1202. Suggested dimensions for the perimeter of membrane layer 1204 are, for example, 2 mm x 6 mm. Such dimensions, however, are only referred to here for exemplary and illustrative purposes only and are not considered a limiting feature of the embodiment. Membrane layer 1204 can be configured as a layer of, for example, silicon nitride layer or other membrane materials such as silicon dioxide, oxy-nitride, aluminum nitride, diamond and so forth. A piezoelectric material 1206 (e.g., zinc oxide) can be sputtered onto the surface of the dielectric membrane layer 1204. Finally, IDT metal electrodes (i.e., the IDTs that launch the acoustic wave) 1208 and 1220 can be patterned onto the surface thereof. The last process step is to backside etch the silicon wafer to "release" the membrane 1204.

The thin oxide or nitride membrane 1204 generally possesses a thickness (e.g., < a few microns) much less than that of the acoustic wavelength. The IDT metal electrodes 1208, 1220 on the piezoelectric layer 1206 excite the acoustic mode, much like the waves created with the SAW devices. The acoustic wave propagates from one IDT metal electrodes 1208, 1220 to the other in the delay line fashion. The membrane 1204 motion can be normal to the surface (like a vibrating drumhead) or can propagate a shear wave like in the SH-SAW devices. Any perturbation of the surface changes the propagating wave velocity and damps the acoustic vibration.

A number of advantages can be obtained through the use of FPW devices. For example, the detection sensitivity is not based on frequency of operation like other acoustic devices, but instead on the relative magnitude of the perturbation to a parameter of the membrane. In the case of mass, the sensitivity is the ratio of the added mass to the membrane mass. Since very thin (low mass) membranes can be created, the detection sensitivities can be very large, much larger than other acoustic sensor modes. Frequencies of operation are in 100's of kHz to few MHz range. The low operating frequency leads to simple electronic circuits to drive and detect sensor signals.

Because the FPW devices are made on silicon wafers, large arrays of the devices can be fabricated on single substrates. And all of the drive and detection electronics can be integrated onto the same substrate. For large scale sensor system integration, the FPW devices are one of the only acoustic technologies available. The antibody films and fluids for bio-sensing are contact the etched silicon side of the device. This provides a natural fluid barrier to protect the metals and other electronics that are placed on the far surface. Integrated silicon electronic devices can be very low cost and are easily packaged.

Figure 13:
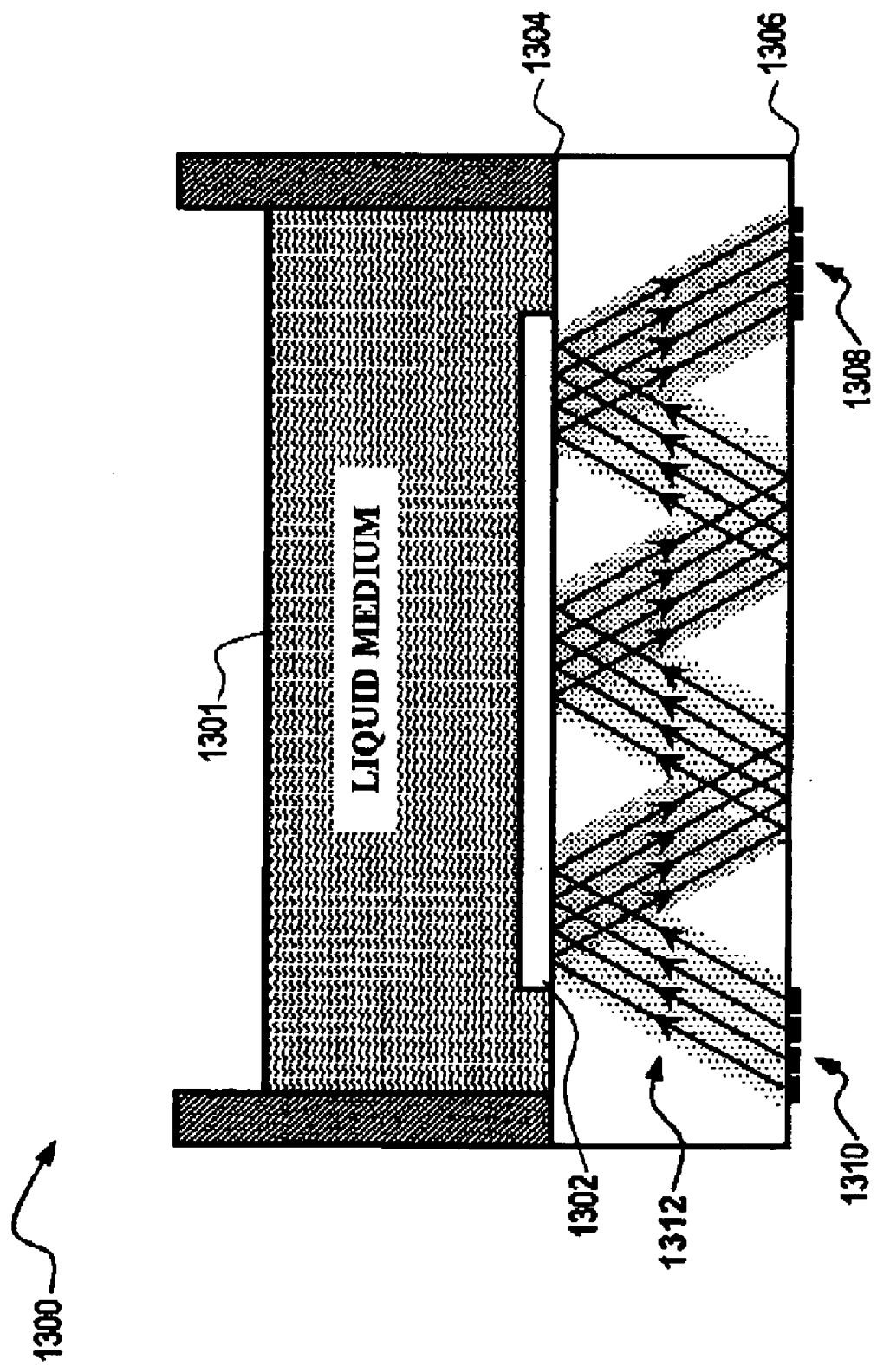
FIG. 13 illustrates an APM sensor that interacts with a liquid medium, which can be adapted in accordance with an alternative embodiment.

FIG. 13 illustrates an APM sensor 1300 that interacts with a liquid medium 1301, which can be adapted in accordance with an alternative embodiment. The liquid medium 1301 may be, for example, engine oil. APM and FPW employ similar principles as SAW and TSM, but exploit different modes of elastic wave propagation. The mass sensitivity of a ST quartz APM device in liquid is approximately 6% less than that of in vacuum. The higher mass sensitivity of the APM device enables it to function as a general purpose detector, serving as a microbalance in many sensor applications. A sensitive coating 1302 of chemicals on the APM surface enables it to selectively bind species from solution. APM Sensor 1300 generally includes a plurality of interdigital transducers 1308, 1310 configured on a wave generation and reception surface 1306 in association with a wave perturbation surface 1304. The motion of the waves 1312 are indicated in FIG. 13.

Species that are strongly bound move synchronously with the oscillating APM device surface and perturb the oscillating frequency, leading to a sensor response. A major problem encountered with the APM based sensors is "mode hopping". Acoustic plate modes are actually a set of waves that cause the crystal to oscillate at a number of slightly different frequencies simultaneously. These frequencies are called modes. As the mass loading is increased, the modes will all shift to a lower frequency. A resonator circuit tuned to one mode can track that frequency peak until mass loading causes the next higher mode to become close enough to the tuned frequency of the resonator circuit. At this point the resonator can lock onto the next higher mode and the frequency output by the circuit in response to increased mass will appear to jump to a higher frequency. This is known as "mode hopping". Problems associated with mode hopping have seriously limited the performance of sensors made based on bulk modes.

Shear-horizontal acoustic plate mode (SH-APM) sensors have been developed for sensing in the liquid. SH modes have particle displacement mainly parallel to the device surface and normal to the direction of propagation. The absence of a surface-normal component of displacement allows SH plane mode to propagate in contact with a liquid without coupling excessive amounts of acoustic energy into the liquid. By comparison, when surface acoustic waves are propagated at solid/liquid interface, the surface-normal displacement radiate compressional waves into the liquid and severely attenuate the wave.

SH-APM could use thin quartz plates that serve as acoustic wave-guides, confining acoustic energy between the upper and lower surfaces of the plate as a wave propagates between input and output transducers. While in SAW device, almost all acoustic energy is concentrated within the wavelength of the surface. The consequences of this difference are that the sensitivity of the SH-APM to mass loading and other perturbations depends on the thickness of the quartz. Both surfaces of the device undergo displacement, so the detection can occur on either surface of the device. The APM device generally possesses about the same sensitivity as a TSM-based device.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A wireless oil filter sensing system, comprising:
   an oil filter;
   a sensing mechanism that is connectable to said oil filter, wherein said sensing mechanism comprises at least one bulk acoustic wave sensing element and at least one antenna that communicates with said at least one bulk acoustic wave sensing element, wherein when said at least one bulk acoustic wave sensing element is in contact with oil contained in said oil filter, said at least one bulk acoustic wave sensing element detects acoustic waves associated with said oil in response to an excitation of said at least one bulk acoustic wave sensing element; and
   a pattern recognition module that recognizes varying grades of said oil based on at least one signal transmitted by said antenna thereby generating data indicative of a quality of said oil for wireless transmission through said at least one antenna.

2. The system of claim 1 wherein said excitation of said at least one bulk acoustic wave sensing element occurs in response to at least one wireless signal transmitted to said at least one antenna.

3. The system of claim 1 wherein said acoustic waves associated with said oil comprise flexural plate waves.

4. The system of claim 1 further comprising a receiver which communicates with said sensing mechanism and said pattern recognition module.

5. The system of claim 4 wherein said pattern recognition module identifies a viscosity of said oil based on said at least one signal transmitted by said antenna.

6. The system of claim 4 wherein said pattern recognition module identifies a degradation of said oil based on said at least on signal transmitted by said antenna.

7. The system of claim 1 wherein said data indicative of a quality of said oil comprises phase and amplitude data.

8. The system of claim 4 wherein said data indicative of a quality of said oil comprises phase and amplitude data.

9. The system of claim 1 wherein said at least one bulk acoustic wave sensing element comprises a flexural plate wave (FPW) sensing element.

10. A wireless oil filter sensing system, comprising:
an oil filter; and
a sensing mechanism that is connectable to said oil filter, wherein said sensing mechanism comprises at least one bulk acoustic wave sensing element and at least one antenna that communicates with said at least one bulk acoustic wave sensing element, wherein when said at least one bulk acoustic wave sensing element is in contact with oil contained in said oil filter, said at least one bulk acoustic wave sensing element detects acoustic waves associated with said oil in response to an excitation of said at least one bulk acoustic wave sensing element, thereby generating phase and amplitude data indicative of a quality of said oil for wireless transmission through said at least one antenna and wherein said excitation of said at least one acoustic wave sensing element occurs in response to at least one wireless signal transmitted to said antenna; and
a pattern recognition module that based on said at least one signal transmitted by said antenna recognizes varying grades of said oil based on at least one signal transmitted by said antenna, identifies a viscosity of said oil, and identifies a degradation of said oil.

11. The system of claim 10 wherein said acoustic waves associated with said oil comprise flexural plate waves.

12. A wireless oil filter sensing method, comprising:
providing an oil filter;
connecting a sensing mechanism to said oil filter, wherein said sensing mechanism comprises at least one bulk acoustic wave sensing element and at least one antenna that communicates with said at least one bulk acoustic wave sensing element, wherein when said at least one bulk acoustic wave sensing element is in contact with oil contained in said oil filter, said at least one bulk acoustic wave sensing element detects acoustic waves associated with said oil in response to an excitation of said at least one bulk acoustic wave sensing element, thereby generating phase and amplitude data indicative of a quality of said oil for wireless transmission through said at least one antenna; and
utilizing a pattern recognition module to recognize varying grades of said oil based on at least one signal transmitted by said at least one antenna.

13. The method of claim 12 further comprising transmitting at least one wireless signal transmitted to said at least one antenna in order to excite said at least one bulk acoustic wave sensing element.

14. The method of claim 12 wherein said acoustic waves associated with said oil flexural plate waves.

15. The method of claim 12 further utilizing a pattern recognition module to recognize varying grades of said oil based on at least one signal transmitted by said at least one antenna.

16. The method of claim 15 wherein said pattern recognition module identifies a viscosity of said oil based on said at least one signal transmitted by said at least one antenna.

17. The method of claim 15 wherein said pattern recognition module identifies a degradation of said oil based on said at least on signal transmitted by said at least one antenna.

18. The method of claim 12 further comprising configuring said at least one bulk acoustic wave sensing element to comprises a flexural plate wave (FPW) sensing element.

19. The method of claim 12 further comprising:
providing an interrogator comprising a transmitter and a receiver;
transmitting from said transmitter of said interrogator at least one signal in order to excite said at least one bulk acoustic wave sensing element to vibrate in at least one desired mode thereof through at least one antenna; and
receiving at said receiver at least one signal transmitted from said at least one bulk acoustic wave sensing element.

20. The method of claim 12 further comprising:
providing at least one antenna connected to said at least one bulk acoustic wave sensing element, such said at least one antenna receives at least one excitation signal in order to permit said at least one bulk acoustic wave sensing element to vibrate in at least one desired mode upon receipt of said excitation signals from an interrogator; and
transmitting from at least one antenna associated with said at least one bulk acoustic wave sensor, said data indicative of the quality of said engine oil to a receiver associated with an interrogator for receiving and collecting said data.

21. The method of claim 12 wherein said at least one antenna comprises at least one of the following types of antennas: a linear type antenna or a coupler type antenna.

* * * * *

UNITED STATES PATENT AND TRADEMARK OFFICE
CERTIFICATE OF CORRECTION

PATENT NO. : 7,287,431 B2 Page 1 of 1
APPLICATION NO. : 11/107099
DATED : October 30, 2007
INVENTOR(S) : James ZT Liu et al.

It is certified that error appears in the above-identified patent and that said Letters Patent is hereby corrected as shown below:

In Column 11, line 3, delete "on" and add --one--.

Signed and Sealed this

Eighth Day of April, 2008

JON W. DUDAS
*Director of the United States Patent and Trademark Office*